US00PP26848P2

(12) United States Plant Patent
Hofmann

(10) Patent No.: US PP26,848 P2
(45) Date of Patent: Jun. 21, 2016

(54) ***EUPHORBIA* PLANT NAMED 'INEUPDIDAZ'**

(50) Latin Name: *Euphorbia hypericifolia*
Varietal Denomination: Ineupdidaz

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 21 days.

(21) Appl. No.: 14/121,807

(22) Filed: Oct. 20, 2014

(51) Int. Cl.
*A01H 5/02* (2006.01)

(52) U.S. Cl.
USPC ..... Plt./302

(58) Field of Classification Search
USPC ..... Plt./302
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Euphorbia* plant named 'Ineupdidaz', characterized by its upright and mounded plant habit; vigorous growth habit; freely branching habit; freely flowering habit; and inflorescences with multiple white-colored flower bracts.

1 Drawing Sheet

Botanical designation: *Euphorbia hypericifolia.*
Cultivar denomination: 'INEUPDIDAZ'.

BACKGROUND OF THE INVENTION

The present invention relates to a new and distinct cultivar of *Euphorbia* plant, botanically known as *Euphorbia hypericifolia* and hereinafter referred to by the name 'Ineupdidaz'.

The new *Euphorbia* plant is a product of a planned breeding program conducted by the Inventor in Heidesheim, Germany. The objective of the program is to create and develop new *Euphorbia* plants with upright plant habit and multiple white-colored flower bracts per inflorescence.

The new *Euphorbia* plant originated from a cross-pollination by the Inventor in July, 2011 of a proprietary selection of *Euphorbia hypericifolia* identified as code number ch10-2100-10, not patented, as the female, or seed, parent with a proprietary selection of *Euphorbia hypericifolia* identified as code number ch10-2101-21, not patented, as the male, or pollen, parent. The new *Euphorbia* plant was discovered and selected by the Inventor as a single flowering plant within the progeny of the stated cross-pollination in a controlled greenhouse environment in Heidesheim, Germany in August, 2012.

Asexual reproduction of the new *Euphorbia* plant by terminal vegetative cuttings in a controlled greenhouse environment in Gensingen, Germany since October, 2012 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Ineupdidaz'. These characteristics in combination distinguish 'Ineupdidaz' as a new and distinct *Euphorbia* plant:

1. Upright and mounded plant habit.
2. Vigorous growth habit.
3. Freely branching habit.
4. Freely flowering habit.
5. Inflorescences with multiple white-colored flower bracts.

Plants of the new *Euphorbia* differ primarily from plants of the female parent selection in the following characteristics:

1. Plants of the new *Euphorbia* have more flower bracts per inflorescence than plants of the female parent selection.
2. Plants of the new *Euphorbia* and the female parent selection differ in flower bract color as plants of the female parent selection have grey-colored flower bracts.

Plants of the new *Euphorbia* differ primarily from plants of the male parent selection in the following characteristics:

1. Plants of the new *Euphorbia* are more compact than plants of the male parent selection.
2. Plants of the new *Euphorbia* are more freely branching and denser than plants of the male parent selection.
3. Plants of the new *Euphorbia* flower earlier than plants of the male parent selection.

Plants of the new *Euphorbia* can be compared to plants of the *Euphorbia hypericifolia* 'Inneuphdia', disclosed in U.S. Plant Pat. No. 17,567. In side-by-side comparisons conducted in Heidesheim, Germany, plants of the new *Euphorbia* differed from plants of 'Inneuphdia' in the following characteristics:

1. Plants of the new *Euphorbia* were more compact than plants of 'Inneuphdia'.
2. Plants of the new *Euphorbia* were more freely branching than plants of 'Inneuphdia'.
3. Plants of the new *Euphorbia* had more flower bracts per inflorescence than plants of 'Inneuphdia'.

Plants of the new *Euphorbia* can also be compared to plants of the *Euphorbia hypericifolia* 'Balbrewite', disclosed in U.S. Plant Pat. No. 21,439. In side-by-side comparisons conducted in Heidesheim, Germany, plants of the new *Euphorbia* differed from plants of 'Balbrewite' in the following characteristics:

1. Plants of the new *Euphorbia* were not as compact as plants of 'Balbrewite'.
2. Plants of the new *Euphorbia* were not as freely branching as plants of 'Balbrewite'.
3. Plants of the new *Euphorbia* had more flower bracts per inflorescence than plants of 'Balbrewite'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the bottom of the sheet comprises a side perspective view of a typical flowering plant of 'Ineupdidaz' grown in a container.

The photograph at the top of the sheet is a close-up view of a typical flowering plant of 'Ineupdidaz'.

DETAILED BOTANICAL DESCRIPTION

Plants used in the aforementioned photographs and herewith described in detail were grown in 11.5-cm containers during the spring in an outdoor shadehouse in Bonsall, Calif. and under cultural practices typical of commercial *Euphorbia* production. During the production of the plants, day temperatures averaged 24° C., night temperatures averaged 18° C. and light levels averaged 4,000 foot-candles. Plants were grown under long day/short night photoinductive conditions to initiate flower development. Plants were pinched one time and were four weeks from planting when the photographs and the description were taken. In the following description, color references are made to The Royal Horticultural Society Colour Chart, Fourth Edition, 2007, except where general terms of ordinary dictionary significance are used.

Botanical classification: *Euphorbia hypericifolia* 'Ineupdidaz'.

Parentage:

*Female, or seed, parent*.—Proprietary selection of *Euphorbia hypericifolia* identified as code number ch10-2100-10, not patented.

*Male, or pollen, parent*.—Proprietary selection of *Euphorbia hypericifolia* identified as code number ch10-2101-21, not patented.

Propagation:

*Type*.—Terminal vegetative cuttings.

*Time to initiate roots, summer*.—About eight to ten days at temperatures about 24° C.

*Time to initiate roots, winter*.—About ten to twelve days at temperatures about 21° C.

*Time to produce a rooted young plant, summer*.—About three weeks at temperatures about 24° C. to 27° C.

*Time to produce a rooted young plant, winter*.—About four weeks at temperatures about 21° C. to 24° C.

*Root description*.—Fine, fibrous; white in color.

*Rooting habit*.—Moderately freely branching; medium density.

Plant description:

*Plant and growth habit*.—Upright to outwardly spreading and mounded plant habit; inflorescences positioned above and beyond the foliar plane; vigorous growth habit.

*Branching habit*.—Freely branching habit; when pinched, about four primary lateral branches each with about six secondary lateral branches develop.

*Plant height*.—About 18 cm.

*Plant diameter or spread*.—About 25 cm.

*Lateral branch description*.—Length: About 16 cm. Diameter: About 2.5 mm. Internode length: About 3.4 cm. Aspect: Mostly upright to outwardly. Strength: Moderately strong. Texture: Smooth, glabrous. Color: Close to 146A; at the nodes, blushed with close to 182B.

*Leaf description*.—Arrangement: Alternate, simple. Length: About 3 cm. Width: About 9 mm. Shape: Elliptical. Apex: Rounded. Base: Attenuate. Margin: Entire. Venation pattern: Pinnate, arcuate. Texture, upper surface: Smooth, glabrous. Texture, lower surface: Sparsely pubescent. Color: Developing leaves, upper surface: Close to 137A. Developing leaves, lower surface: Close to 137C. Fully developed leaves, upper surface: Close to N137B; venation, close to N137B. Fully developed leaves, lower surface: Close to 137C; venation, close to 137C. Petioles: Length: About 2 cm. Diameter: Less than 1 mm. Texture, upper and lower surfaces: Sparsely pubescent. Color, upper and lower surfaces: Close to 146C.

Inflorescence description:

*Inflorescence type and habit*.—Inflorescences are composed of a single cyathia surrounded with numerous flower bracts subtending the cyathia; inflorescences positioned above and beyond the foliar plane; numerous inflorescences develop per plant.

*Inflorescence diameter*.—About 1 cm.

*Inflorescence height*.—About 3 mm.

*Fragrance*.—None detected.

*Natural flowering season*.—Plants typically flower from the spring until the autumn in southern California.

*Inflorescence longevity*.—Inflorescences last about four to five days on the plant.

*Flower bracts*.—Quantity per inflorescence: About five to ten. Length, largest bracts: About 6 mm. Width, largest bracts: About 2 mm. Shape: Narrowly spatulate. Apex: Rounded to broadly acute. Base: Attenuate. Margin: Entire. Texture, upper surface: Smooth, glabrous. Texture, lower surface: Slightly pubescent. Aspect: Mostly horizontal. Venation pattern: Pinnate, arcuate. Color: Developing and fully expanded bracts, upper surface: Close to NN155D. Developing and fully expanded bracts, lower surface: Close to NN155D. Flower bract petioles: Length: About 2 mm. Diameter: Less than 1 mm. Texture, upper and lower surfaces: Smooth, glabrous. Color, upper and lower surfaces: Close to 145C.

*Cyathia*.—Quantity per corymb: One. Diameter: About 2 mm. Height: About 2 mm. Shape: Globose; sessile. Color: Close to 144A. Nectaries: Nectary development has not been observed on plants of the new *Euphorbia*.

*Peduncles*.—Length: About 2 mm. Diameter: Less than 1 mm. Strength: Moderately strong. Aspect: Upright. Texture: Smooth, glabrous. Color: Close to 145A.

*Reproductive organs*.—Stamens: Stamen development has not been observed on plants of the new *Euphorbia*. Pistils: Quantity per cyathia: One. Pistil length: About 1 mm. Stigma shape: Five to six-parted. Stigma color: Close to NN155D. Style length: Less than 1 mm. Style color: Close to NN155D. Ovary color: Close to 144A.

*Seeds and fruits*.—Seed and fruit production has not been observed on plants of the new *Euphorbia*.

Disease & pest resistance: Plants of the new *Euphorbia* have not been shown to be resistant to pathogens and pests common to *Euphorbia* plants.

It is claimed:

1. A new and distinct *Euphorbia* plant named 'Ineupdidaz' as illustrated and described.

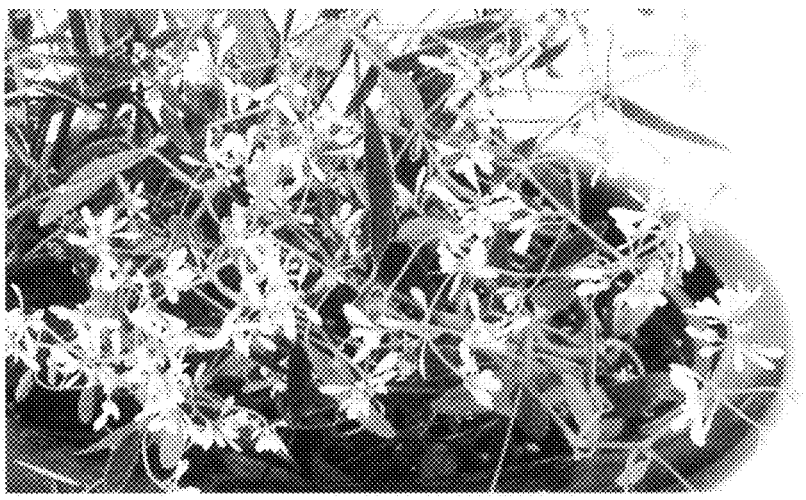
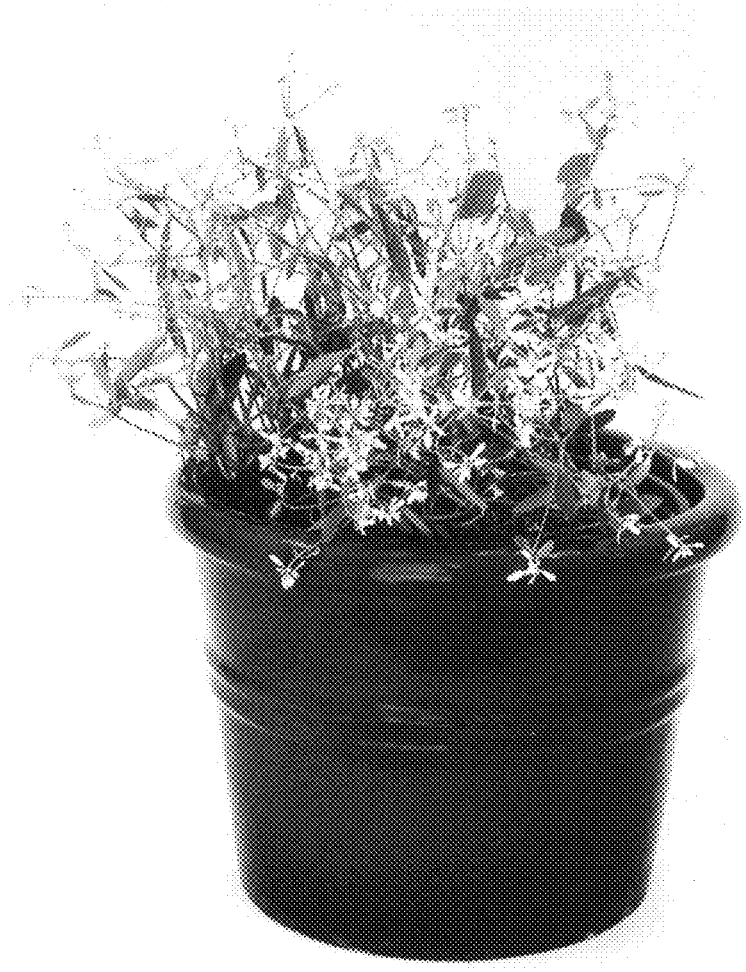

* * * * *